United States Patent [19]

Tateishi

[11] 4,277,828
[45] Jul. 7, 1981

[54] ANALYZER FOR RESULTANT FORCE AT JOINT

[75] Inventor: Tetsuya Tateishi, Higashi-Murayama, Japan

[73] Assignees: Agency of Industrial Science & Technology; Ministry of International Trade & Industry, both of Tokyo, Japan

[21] Appl. No.: 86,687

[22] Filed: Oct. 19, 1979

[30] Foreign Application Priority Data

Oct. 24, 1978 [JP] Japan .............................. 53-1300760

[51] Int. Cl.³ ............................................. A61B 5/00
[52] U.S. Cl. .................................. 364/415; 364/413; 128/774
[58] Field of Search ....................... 364/413, 415, 508; 128/774, 779, 781, 782; 33/1 M, 1 C

[56] References Cited

U.S. PATENT DOCUMENTS

| 4,135,498 | 1/1979 | McGee | 128/774 |
| 4,195,643 | 4/1980 | Pratt, Jr. | 128/779 |
| 4,201,226 | 5/1980 | Phillips | 128/774 |

Primary Examiner—Charles E. Atkinson
Assistant Examiner—Gary Chin
Attorney, Agent, or Firm—Kurt Kelman

[57] ABSTRACT

An analyzer for determining the resultant force at a bone joint has a pair of cursors which are successively set to crucial points on an X-ray picture of the bone joint. The cursors are connected to potentiometers which produce signals corresponding to their positions. The signals are fed to a data processing unit which calculates the resultant force from a known formula.

2 Claims, 3 Drawing Figures

ANALYZER FOR RESULTANT FORCE AT JOINT

BACKGROUND OF THE INVENTION

This invention relates to an apparatus for the analysis of the resultant force at a joint in a human or animal body.

Recently, in the field of orthopedic surgery or other similar branches of medicine, there has been frequently felt the necessity of analyzing the resultant force at a joint. In the case of a patient whose hip joint has been replaced with an artificial joint, for example, if the value of the resultant force at the artificial joint calculated after the surgery exceeds 3.5 times the body weight of the patient, the joint will be deficient in load bearing capacity so that the joint will, more often than not, be unable to recover its normal function. For this reason, it is quite important from the clinical point of view to analyze the magnitude and direction the resultant force exerts at the joint before and after the surgery for total joint replacement. The resultant force at the joint has heretofore been determined by use of a pedestrian analyzer or by a method which utilizes a transducer inserted in the patient's body and a telemeter installed separately to receive and analyze data from the transducer. These devices are invariably expensive and cannot be easily operated because they involve highly advanced electronic technology. Under the circumstances, clinical practitioners specializing in orthopedic surgery are compelled to reckon the resultant forces at the joints on the basis of figures drawn from X-ray images of the joints. Generally it is difficult to insert lines on the X-ray films, and an effort to print a new X-ray picture and draw figures from the X-ray picture entails a great deal of work. Another possible method involves the drawing of an X-ray image on a monitor with a light pen. The actual operation of this method, however, requires use of an expensive image analyzer.

A primary object of this invention, therefore, is to provide an analyzer for the resultant force at a joint, which is inexpensive and can be easily operated by any person, skilled or unskilled.

SUMMARY OF THE INVENTION

To accomplish the object described above according to the present invention, there is provided an analyzer for the resultant force at a joint, which analyzer comprises a table possessing an optically pervious top plate suitable for spreading thereon a sheet containing the picture image of a given joint, a pair of cursors disposed on the table top and adapted to be freely slid in the longitudinal and lateral driections of the table top, a pair of potentiometers adapted to generate potential signals corresponding to the positions of the cursors relative to the table top and data processing means adapted to calculate the resultant force at the joint on the basis of the potential signals representing crucial points of the picture image of the joint and issuing from the potentiometers.

The analyzer for the resultant force at the joint according to this invention is not expensive because it is obtained simply by attaching the pair of cursors and the pair of potentiometers to an ordinary device for visual observation of X-ray films and connecting the potentiometers to a small computer. This analyzer permits ready analysis of the desired resultant force at the joint by tracing with the cursors only the crucial points on the X-ray film and thereby allowing the relative values at such points to be stored in the computer and then operating the computer in accordance with a fixed formula of calculation.

The other objects and characteristics of the present invention will become apparent from the following detailed description of the invention, taken in conjunction with the accompanying drawing.

DESCRIPTION OF PREFERRED EMBODIMENT

There have been proposed numerous formulas for the calculation of the resultant forces at the various joints in the human body. The formulas proposed by different researchers for application to one and the same joint may be slightly at variance. By whatever means the relative values at the crucial points of the joint necessary for the formula are obtained, the resultant force at that joint can be readily determined by applying these relative values to the formula.

Figure 1:
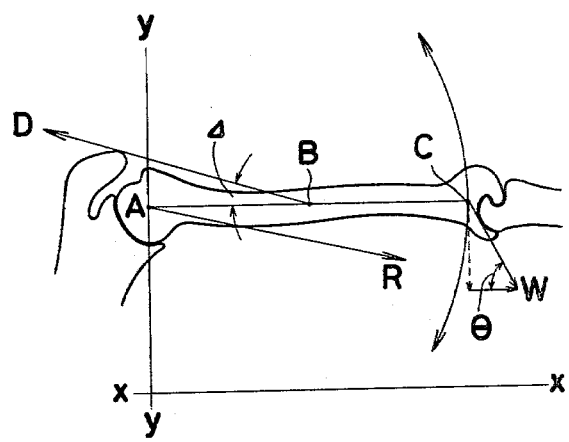
FIG. 1 is an explanatory diagram illustrating the directions of the muscular force and the resultant force at a shoulder joint.

In the case of the shoulder joint illustrated in FIG. 1, for example, maintenance of equilibrium at the joint dictates a requirement that the three forces, i.e. the weight of the upper limb "W", the force of the triangularis "D" and the resultant force "R", should be well balanced. The weight of the upper limb is assumed to account for 9% of the total body weight. When the relative values at the point of action "C" of the weight of the upper limb, the center of the ball joint "A" of the humerus bone and the point of action "B" of the force of the triangularis are determined in conjunction with the angles $\theta$ and $\Delta$, the force of the triangularis and the resultant force "R" can be calculated in accordance with the following formulas.

$$D = \frac{a \sin \theta}{b \sin \Delta} \times W$$

$$R = \sqrt{\frac{a \sin \theta}{b \sin \Delta} - 2 \frac{a \sin \theta}{b \sin \Delta} \cos\phi + 1} \times W$$

In the formulas given above, "a" stands for the distance $\overline{AC}$, "b" for the distance $\overline{AB}$ and "$\phi$" for the difference ($\theta - \Delta$) between the angle $\theta$ and the angle $\Delta$.

In the case of the shoulder joint described above, therefore, the resultant force at the shoulder joint can readily be calculated from the formula shown above when the relative values at the points "A", "B" and "C" and the angles $\theta$ and $\Delta$ are determined.

In view of this fact, I have developed an apparatus capable of readily determining the relative values at the crucial points of the joint and the angles which are required for the calculation of the resultant force at the joint. The analyzer of this invention will be specifically described below with reference to FIG. 2.

Figure 2:
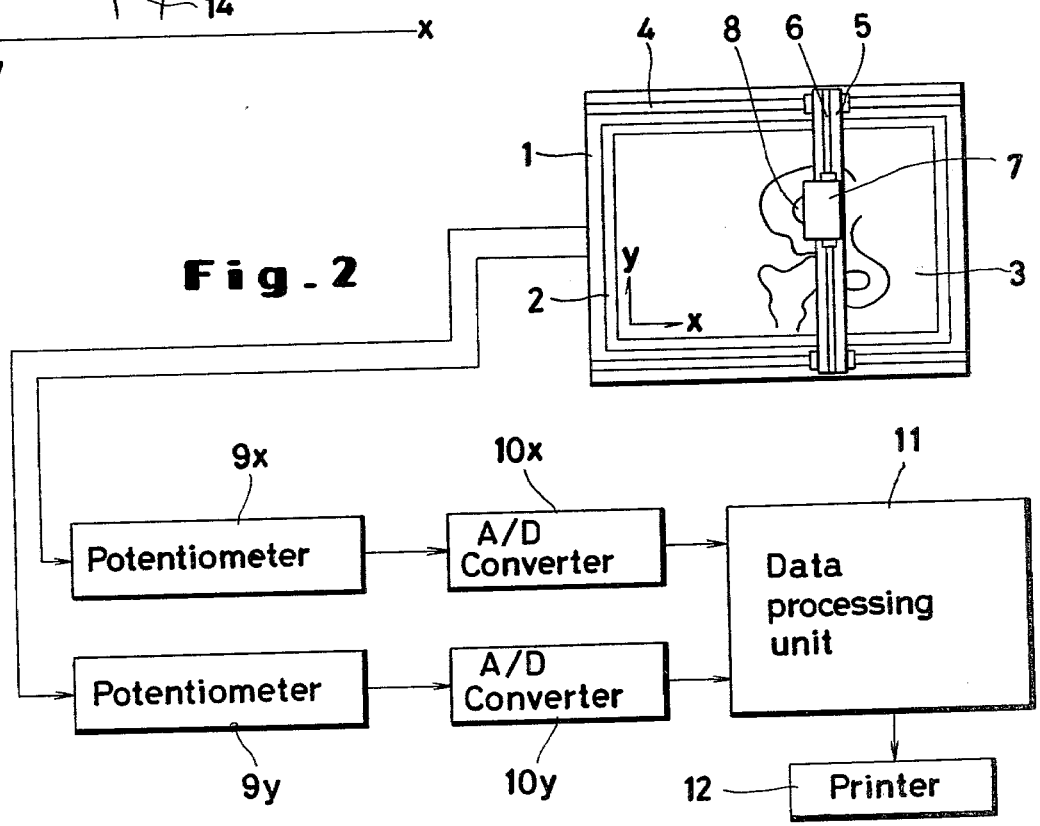
FIG. 2 is a structural diagram illustrating one embodiment of the analyzer for the resultant force at the joint according to the present invention.

With reference to FIG. 2, a top plate 2 in a table 1 consists of a transparent or translucent glass plate. X-ray film 3 may be held on glass top plate 2 and the image on the X-ray film 3 may be visually inspected by means of the light from a light source (not shown) concealed inside the enclosure of the table 1 and passing through the glass top plate 2 to reach the viewer. Two parallel X-axis rails 4 extend along the opposite longitudinal edges of the table top throughout the entire length. An X-cursor 5 is freely slidably mounted on the pair of X-axis rails. The X-cursor 5 supports thereon a Y-axis rail 6. A Y-cursor 7 which is freely slidably mounted on this Y-axis rail 6 is provided with a graph pen 8 to be used for tracing the crucial points of the image on the X-ray film 3. A potentiometer 9x is connected to the X-cursor 5 and a potentiometer 9y to the Y-cursor 7 by mechanical means (not shown), for example. When the graph pen 8 is brought into contact with a given point on the X-ray film, the potentiometers 9x, 9y generate potential signals representing the positions of the X-cursor and Y-cursor. Since these potential signals are of an analogous form, they are converted through their respective A/D converters 10x, 10y into digital signals for the sake of simplicity in the subsequent processing and the digital signals are forwarded to a data processing unit 11. When the data processing unit 11 is of a type capable of directly processing analog signals, no converter is needed. On the basis of the digital input signals representing the relative values at the crucial points of the joint, the data processing unit performs an arithmetic operation to determine the resultant force, muscular force, etc. at the joint and prints out or displays the results on a printer 12 which is connected to the output of unit 11. An ordinary electronic computer can be used as the data processing unit.

Specifically, in determining the values at specific points on the X-ray film in actual practice, the potential signals for any pair of freely chosen positions of the X-cursor and Y-cursor on the X-ray are first stored in the data processing unit as standard potentials. Then the X-cursor and Y-cursor are sequentially set at the crucial points on the X-ray film of the joint under test, and the corresponding potential signals are fed to the data processing unit where they are compared with the standard potentials to find the potential differences between the potential signals for the crucial points and those for the standard points.

Now, the operation of the aforementioned analyzer for the resultant force at the joint as applied to the analysis of the resultant force at the hip joint will be described with reference to FIG. 3.

Figure 3:
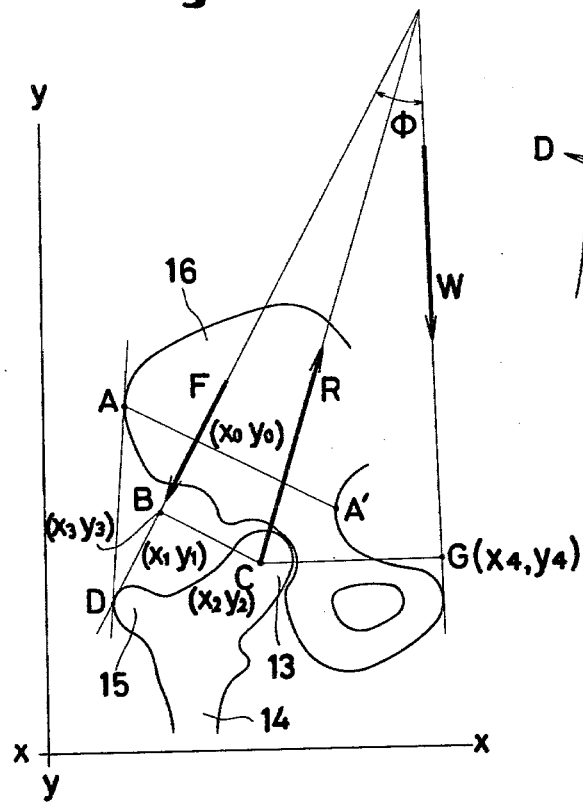
FIG. 3 is an explanatory diagram illustrating the directions of the resultant force, the muscular force and force of gravity at the hip joint.

In the determination of the total muscular force "F" exerted by the group of abductors at the hip joint and the resultant force "R" exerted upon the head of the femur illustrated in FIG. 3, the magnitudes of the muscular force "F" and the resultant force "R" are calculated in accordance with the following formulas (1) and (2) respectively.

$$F = \frac{a}{b} \cdot W \tag{1}$$

$$R = \sqrt{(\frac{a}{b})^2 + 2(\frac{a}{b})\cos\phi + 1} \times W \tag{2}$$

In the foregoing formulas, "W" stands for the body weight, "a" for the length of the perpendicular line $\overline{CG}$ extending from the central point "C" of the head 13 of the femur to the line indicating the direction of the body weight "W", "b" for the length of the perpendicular line $\overline{BC}$ extending from the central point "C" of the head 13 of the femur to the line indicating the direction of muscular action of the abductor and "$\phi$" for the angle formed between the line tangential to the great trochanter 15 of the femur 14 and the line indicating the direction of the body weight "W".

Preparatory to the analyzer's operation, an X-ray film 3 containing the image of the joint under test is fastened to the upper surface 2 of the table 1 so that the image can be visually inspected with the light issuing from the light source concealed under the top plate of the table 1 and passing through X-ray film 3 to reach the viewer. As occasion demands, the X-ray film 3 may be covered with a transparent sheet capable of being marked with a proper writing implement. At the same time, the body weight "W" is measured and stored in advance in the data processing unit 11. Then, the potential signals representing a point taken to serve as the standard point of the X-Y coordinate system on the X-ray film are converted through A/D converters 10x, 10y into corresponding digital signals, which are introduced as the input to the data processing unit. This completes the preparatory step. Then the analyzer is operated by following the procedure to be described below, to determine the resultant force "R" and the muscular force "F".

(1) The direction "$\phi$" of the action of the total musucular force "F" of the group of abductors is determined as follows.

A tangential line $\overline{AD}$ is drawn to include the outermost points of the great trochanter 15 of the femur 14 and the pelvis 16 and a line $\overline{AA'}$ is drawn to connect the contact point "A" of the pelvis 16 over the shortest possible distance to the inner wall of the iliac bone as found on the X-ray film. A point about ⅓ the length of the line $\overline{AA'}$ inward from end point "A" of line AA' is taken as the origin of a coordinate system ($X_0$, $Y_0$). By operating the cursors 5, 6, the graph pen 8 is brought into contact with the origin. Consequently, the potentiometers 9x, 9y generate potential signals representing the positions assumed by the cursors on the X-ray film and the potential signals are converted through respective A/D converters 10x, 10y into digital signals, which are fed as input to the data processing unit 11. From the origin ($X_0$, $Y_0$) of the coordinate system, a tangential line is drawn to touch the great trochanter 15. Again by operating the cursors 5, 6, the graph pen 8 is caused to touch a freely selected point ($X_1$, $Y_1$) on this tangential line. Consequently, the potentiometers 9x, 9y generate potential signals representing the positions now assumed by the cursors and the potential signals are likewise subjected to the conversion and fed as input to the data processing unit 11. The data processing unit 11 compares the potential signals representing the points ($X_0$, $Y_0$) and ($X_1$, $Y_1$) of the coordinate system with those of the standard point and registers the respective differences as the values representing the aforementioned points. By further operation of the data processing unit, the angle $\phi$ formed between the extension "F" of the line connecting the point "D" to the origin ($X_0$, $Y_0$) and the line "W" showing the direction of the body weight is calculated in accordance with the following formula.

$$\phi = 90° - \tan^{-1} \frac{Y_0 - Y_1}{X_0 - X_1}$$

(2) Then, the center "C" of the head 13 of the femur 14 is determined. It is fixed substantially at the center of the circular portion of the head 13. By operating the cursors 5, 7, the graph pen 8 is caused to touch the point "C" ($X_2$, $Y_2$). Consequently, the potentiometers 9x, 9y generate pontential signals representing the positions assumed by the cursors and introduce these potential signals into the data processing unit 11. The data processing unit 11 compares these potential signals with those representing the standard point of the coordinate system and stores the differences as the values representing the point "C".

(3) From the point "C", a perpendicular line $\overline{CB}$ is drawn to the line "F". By operating the cursors 5, 7, the graph pen 8 is caused to touch the point B ($X_3$, $Y_3$) which is the foot of the perpendicular line on the line "F". The potentiometers 9x, 9y again generate potential signals representing the positions assumed by the cursors and introduce these potential signals into the data processing unit 11. Consequently, the data processing unit compares these potential signals with those of the standard point and registers the differences as the values representing the aforementioned point "B". The length "b" of the perpendicular line $\overline{BC}$ is calculated by operating the data processing unit 11 in accordance with the following formula.

$$\text{Length } b \text{ of } \overline{BC} = \sqrt{(X_3 - X_2)^2 + (Y_3 - Y_2)^2}$$

(4) From the point "C", another perpendicular line $\overline{CB}$ is drawn to the line showing the direction of the body weight. By operating the cursors and the graph pen, the potentiometers are caused to generate potential signals representing the coordinates ($X_4$, $Y_4$) of the point "G" which is the foot of the perpendicular line $\overline{CB}$ on the line of the direction of gravity and introduce the potential signals into the data processing unit 11, which compares these potential signals with those of the standard point and registers the differences as the values representing the point "G". The length "a" of the perpendicular line $\overline{GC}$ is calculated by operating the data processing unit 11 in accordance with the following formula using the values of the points "C" and "G".

$$\text{Length } a \text{ of } \overline{GC} = \sqrt{(X_4 - X_2)^2 + (Y_4 - Y_2)^2}$$

(5) In consequence of the foregoing steps of processing, the data processing unit 11 has the values of "$\phi$", "a", "b" and "W" registered therein. By the operation of the data processing unit, therefore, the total muscular force "F" exerted by the group of abductors is determined in accordance with Formula (1) and the resultant force "R" exerted on the head of the femur is determined in accordance with Formula (2).

(6) The data processing unit 11 is operated to have the values of "a", "b", "$\phi$", "W", "F", and "R" printed out by the printer 12.

(7) As occasion demands, these values may be used as the input data for a joint simulator (not shown), for example.

As is clear from the foregoing description, the analyzer for the resultant force at a joint according to this invention has been perfected primarily with a view to providing an apparatus so adapted that in all the steps of operation involved, those capable of being easily performed by human hands are left to be manually performed. Consequently, the analyzer is inexpensive and simple in mechanism and permits the determination of the resultant force to be effected with great ease. With this analyzer, the determination of the resultant force or muscular force at a joint under test is accomplished by causing the graph pen to come into contact with the crucial points of the image of the joint on the X-ray film and thereby permitting the potentiometers to generate potential signals corresponding to these points (X-Y coordinate system) and feeding these potential signals, optionally after conversion through A/D converters into digital signals, to the data processing unit and accordingly enabling the data processing unit to compare the potential signals representing the crucial points with those of the standard point of the coordinate system and calculate the resultant force or muscular force in accordance with a prescribed formula using the potential differences so found. Since this analyzer determines the resultant force at the given joint by finding relative values at the crucial points of the image of the joint and applying these values to a formula established for determination of the resultant force as described above, it can be readily utilized with respect to all the joints present in human or animal bodies so far as the formulas for calculation are available. The analyzer is obtained by simply adding cursors and potentiometers to any existing apparatus for see-through inspection of X-ray films and connecting thereto a small computer as the data processing unit. Thus, it permits any clinical practitioner, skilled or unskilled, to determine the resultant force at the joint without necessitating any expensive mechanism or any highly advanced electronic technology.

What is claimed is:

1. An analyzer for the resultant force at a given joint in a human/animal body, which comprises:
    a table provided with a transparent top plate and adapted to support thereon the image of the joint under test,
    a pair of cursors disposed on the table, one adapted to be freely slid on the table in the longitudinal direction and the other adapted to be freely slid on the table in the lateral direction,
    a pair of potentiometers adapted to generate potential signals corresponding to the positions assumed by the cursors on the table, and
    a data processing unit adapted to calculate the resultant force at the joint in accordance with the potential signals issuing from the potentiometers and representing the crucial points of the image of the joint.

2. The analyzer according to claim 1, which further comprises means for converting the potential signals from the potentiometers into digital signals.

* * * * *